(12) United States Patent
Yamaki

(10) Patent No.: US 7,706,820 B2
(45) Date of Patent: Apr. 27, 2010

(54) CONVERSION ADAPTER, MEDICAL SYSTEM AND COMMUNICATION METHOD

(75) Inventor: Masahide Yamaki, Hachioji (JP)

(73) Assignee: Olympus Medical Systems Corporation, Tokyo (JP)

(*) Notice: Subject to any disclaimer, the term of this patent is extended or adjusted under 35 U.S.C. 154(b) by 650 days.

(21) Appl. No.: 11/715,800

(22) Filed: Mar. 8, 2007

(65) Prior Publication Data

US 2007/0233888 A1 Oct. 4, 2007

(30) Foreign Application Priority Data

Mar. 14, 2006 (JP) ............................. 2006-069815

(51) Int. Cl.
*H04B 1/38* (2006.01)
(52) U.S. Cl. ...................................... 455/500; 370/466
(58) Field of Classification Search ................. None
See application file for complete search history.

(56) References Cited

U.S. PATENT DOCUMENTS 6,678,535 B1 * 1/2004 Narayanaswami .......... 455/557

2003/0134590 A1 * 7/2003 Suda et al. .................. 455/3.06
2006/0195613 A1 * 8/2006 Aizu et al. .................. 709/246
2007/0147419 A1 * 6/2007 Tsujimoto et al. ........... 370/466

FOREIGN PATENT DOCUMENTS

JP 2001-144828 5/2001
JP 2005-095567 4/2005

* cited by examiner

*Primary Examiner*—Thanh C Le
(74) *Attorney, Agent, or Firm*—Scully, Scott, Murphy & Presser, P.C.

(57) ABSTRACT

A conversion adapter according to an embodiment of the invention is connected between a control apparatus that controls a medical appliance and the medical appliance and operates as the virtual control apparatus and medical apparatus. Thus, the communication between the control apparatus and medical appliance having different protocols and communication speeds can be performed efficiently. The conversion adapter includes an appliance information managing section, a control section, a first buffer, a second buffer, an appliance-specific command interpreting section, a communication I/F, and a communication I/F.

20 Claims, 13 Drawing Sheets

FIG.6

| No | HIGHER DATA (1 BYTE) | LENGTH | LOWER DATA (2 BYTES) | RESERVATION (VARIABLE LENGTH) | DISPLAY TYPE | OPERATION TYPE |
|---|---|---|---|---|---|---|
| 1 | **** | | | | | |
| 2 | SELECT MODE | | | | | |
| 3 | OUTPUT VALUE SETTING: A | | | | | |
| 4 | OUTPUT VALUE SETTING: B | | | | | |
| 5 | OUTPUT VALUE SETTING: C | | | | | |
| 6 | OUTPUT VALUE SETTING: D | | | | | |
| 7 | ADD NEW FUNCTION | | | | | |
| 8 | ADD NEW FUNCTION | | | | | |

FIG.7

| FUNCTIONS | 1A ELECTRIC KNIFE MANUFACTURED BY A | 1B ELECTRIC KNIFE MANUFACTURED BY B | 1C ULTRASONIC KNIFE MANUFACTURED BY A |
|---|---|---|---|
| SELECT MODE | BI-POLAR MONO-POLAR | BI-POLAR | NORMAL MODE SPECIAL MODE |
| OUTPUT VALUE SETTING: A | 0~400W (STEPS OF 1) | 0~200W (STEPS OF 5) | 0~100W (STEPS OF 10) |
| OUTPUT VALUE SETTING: B | 0~200W (STEPS OF 1) | 0~100W (STEPS OF 5) | 0~100W (STEPS OF 10) |
| OUTPUT VALUE SETTING: C | 0~500W (STEPS OF 1) | 0~600W (STEPS OF 1) | |
| OUTPUT VALUE SETTING: D | 0~500W (STEPS OF 1) | | |
| SPECIAL MODE | NORMAL MODE TEST MODE | | NORMAL MODE TEST MODE |
| SWITCH OUTPUT DESTINATION | REMOTE SWITCH ON/OFF | | SWITCH FOOTSWITCH OUTPUT PATTERN: 1→2→3→4 |

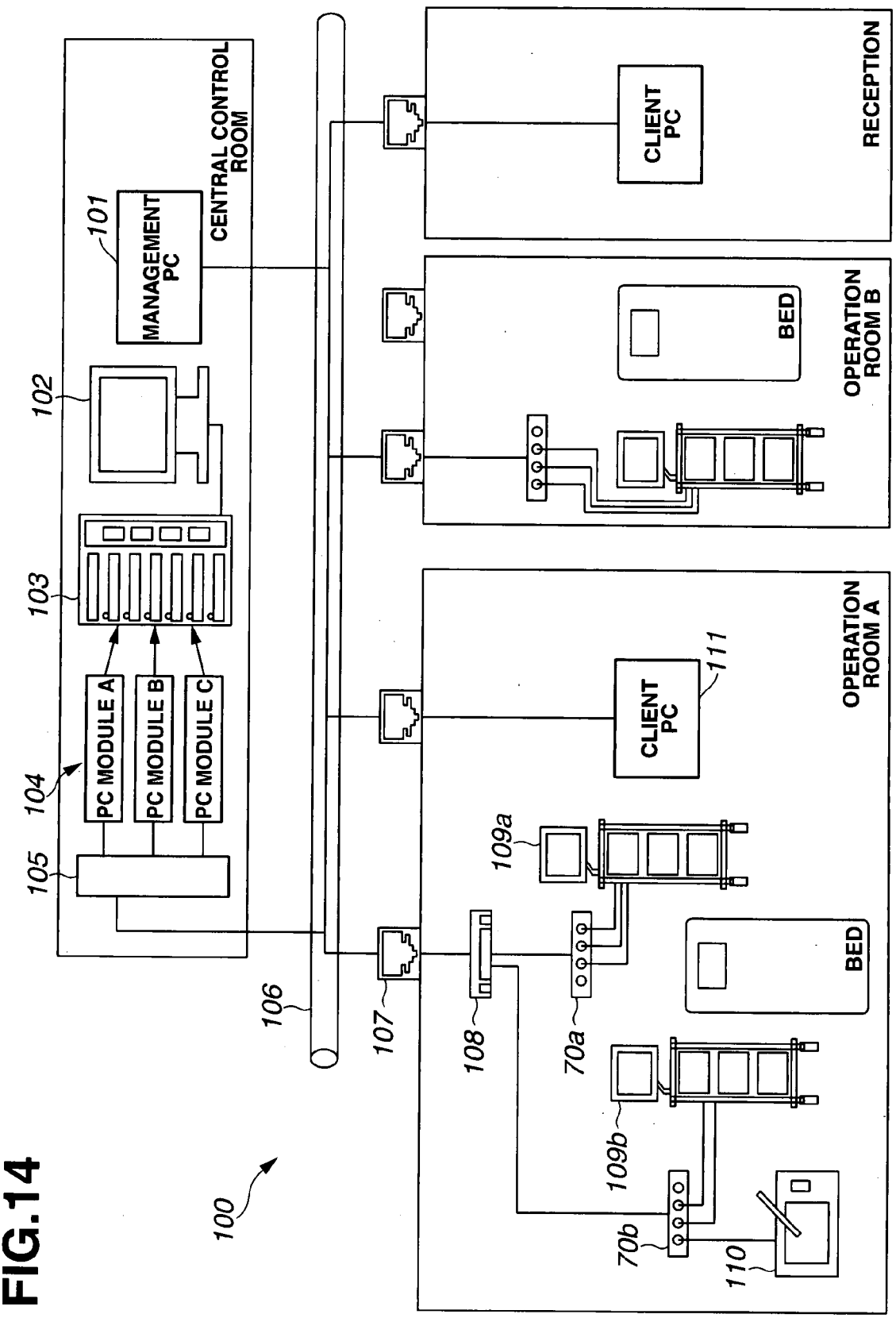

CONVERSION ADAPTER, MEDICAL SYSTEM AND COMMUNICATION METHOD

This application claims benefit of Japanese Application No. 2006-069815 filed in Japan on Mar. 14, 2006, the contents of which are incorporated by this reference.

BACKGROUND OF THE INVENTION

1. Field of the Invention

The present invention relates to a conversion adapter that connects medical appliances and a control apparatus for controlling the medical appliances, a medical system that includes the conversion adapter that connects medical appliances and a control apparatus for controlling the medical appliances, and a communication method for a conversion adapter that connects medical appliances and a control apparatus for controlling the medical appliances.

2. Description of the Related Art

In recent years, various types of medical appliance have been proposed as the medical technologies advance, and the functions of those medical appliances have been expanded. For example, those medical appliances may include an electric knife apparatus, an ultrasonic suction apparatus and laser knife apparatus and so forth. These kinds of medical appliances may be used as a stand-alone basis, or multiple kinds of medical appliances may be used in combination as a medical system.

Such a medical system may connect multiple medical appliances to a control apparatus and centrally control the medical appliances. Japanese Unexamined Patent Application Publication No. 2005-95567 proposes an endoscopic system having a central control apparatus that can connect multiple medical appliances each having a different interface and can reproduce details of a treatment performed during an operation faithfully by reducing a time lag caused between/among the medical appliances.

SUMMARY OF THE INVENTION

According to an aspect of the invention, there is provided a conversion adapter for connecting a control apparatus that controls a medical appliance and the medical appliance, the adapter including a first communication unit for performing communication with the control apparatus based on a first protocol, a second communication unit for performing communication with the medical appliance based on a second protocol, a data extracting unit for extracting communication data from a data signal based on function information associating the data signal received through the first communication unit and the second communication unit and a function information of the medical appliance, a first storage unit for storing the communication data received from the control apparatus based on the first protocol, a second storage unit for storing the communication data received from the medical appliance based on the second protocol, and a control unit for transmitting the communication data stored in the first storage unit to the medical appliance through the second communication unit, transmitting the communication data stored in the second storage unit to the control apparatus through the first communication unit and further transmitting a response signal to the medical appliance through the second communication unit when the communication data is received through the second communication unit.

According to another aspect of the invention, there is provided a medical system having a conversion adapter for connecting a control apparatus that controls a medical appliance and the medical appliance, wherein the conversion adapter has a first communication unit for performing communication with the control apparatus based on a first protocol, a second communication unit for performing communication with the medical appliance based on a second protocol, a data extracting unit for extracting communication data from a data signal based on function information associating the data signal received through the first communication unit and the second communication unit and a function information of the medical appliance, a first storage unit for storing the communication data received from the control apparatus based on the first protocol, a second storage unit for storing the communication data received from the medical appliance based on the second protocol, and a control unit for transmitting the communication data stored in the first storage unit to the medical appliance through the second communication unit, transmitting the communication data stored in the second storage unit to the control apparatus through the first communication unit and further transmitting a response signal to the medical appliance through the second communication unit when the communication data is received through the second communication unit.

According to another aspect of the invention, there is provided a communication method in a conversion adapter for connecting a control apparatus that controls a medical appliance and the medical appliance, the method including a response step of transmitting a response signal to the medical appliance when communication data is received from the medical appliance, a communication data storage step of storing the communication data, a communication data transmission step of transmitting the stored communication data to the control apparatus, an appliance data storage step of storing appliance data when the appliance data is received from the control apparatus, and an appliance data transmission step of transmitting the stored appliance data to the medical appliance at a predetermined timing based on a second protocol.

BRIEF DESCRIPTION OF THE DRAWINGS

FIG. 6 shows an example of the table of command definitions for communication data according to the first embodiment;

FIG. 7 is a diagram showing an example of functions under the category of "electric knife" according to the first embodiment;

FIG. 14 is a schematic configuration diagram of a medical system according to a second embodiment.

DETAILED DESCRIPTION OF THE PREFERRED EMBODIMENTS

Embodiments of the present invention will be described below.

First Embodiment

A conversion adapter according to a first embodiment of the present invention connects multiple medical appliances in a medical system and a control apparatus such as a central control apparatus that can centrally controls the multiple medical appliances. The conversion adapter can convert the interface and protocol of each of the medical appliances to the interface and protocol of the central control apparatus and can efficiently implement the communication between the central control apparatus and the medical appliances. The medical appliance according to the present embodiment refers to a general apparatus used for a medical purpose such as operations. According to the present embodiment, an apparatus such as a VTR and an operation panel is also included in the medical appliance.

Figure 1:
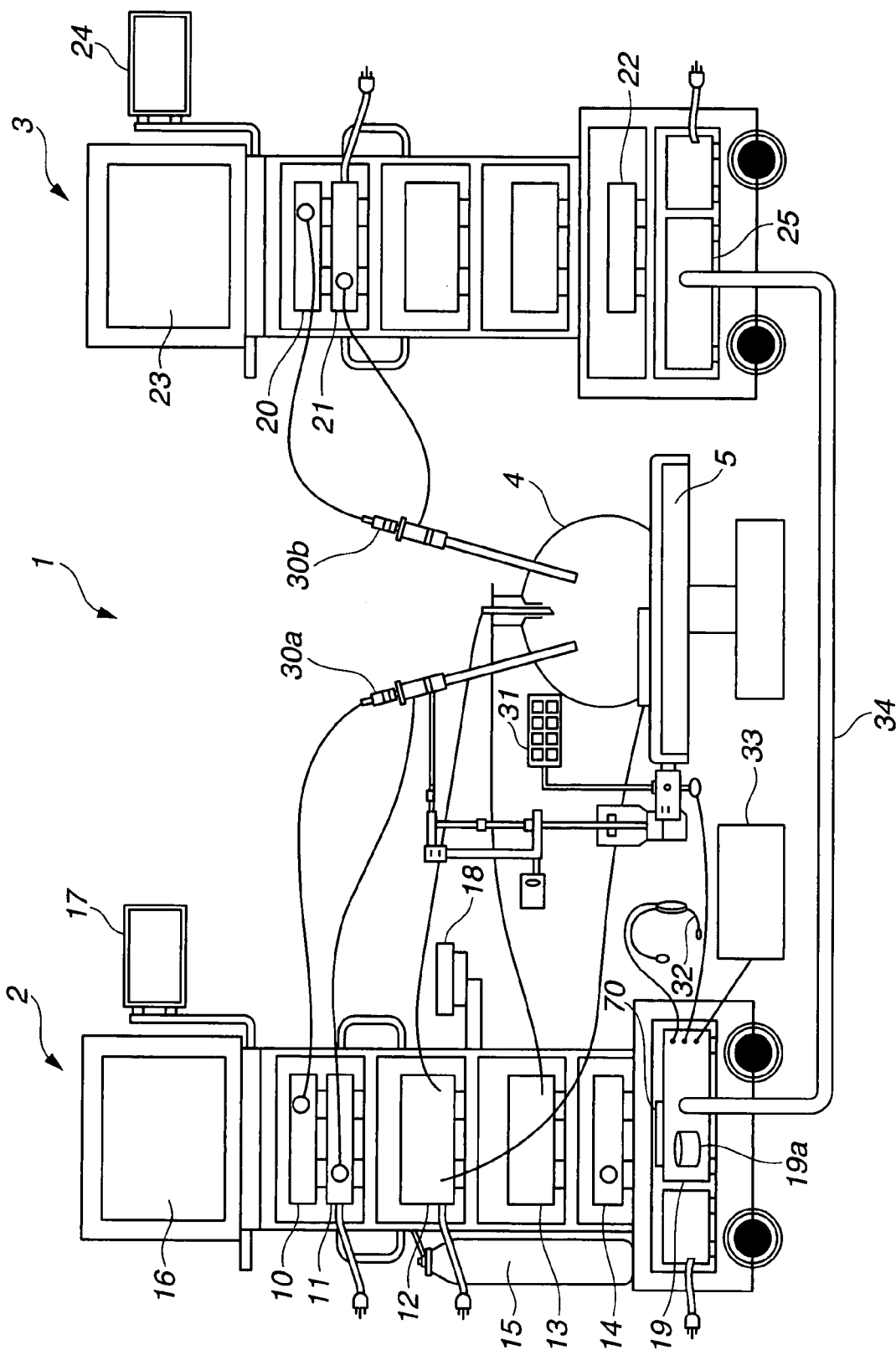
FIG. 1 is a schematic configuration diagram of a medical system according to a first embodiment.

First of all, a medical system including the conversion adapter according to the present embodiment will be described. FIG. 1 is a schematic configuration diagram of a medical system according to a first embodiment. As shown in FIG. 1, a medical system 1 includes a first trolley 2, a second trolley 3 and a bed 5 on which a patient 4 lies down.

The first trolley 2 is a medical appliance including an endoscopic camera control unit (abbreviated to "CCU", hereinafter) 10, a light source device 11, an electric knife apparatus 12, a pneumoperitorium 13, a VTR 14 and a gas cylinder 15.

The first trolley 2 further includes a display device 16, a central display panel 17, and an operation panel 18. The display device 16 is a monitor for displaying an endoscopic image, for example. The central display panel 17 is a display unit that can selectively display any data during an operation. The operation panel 18 includes a display panel such as a liquid crystal display and an input unit such as a touch panel integrally provided on the display panel.

The first trolley 2 further includes a central control apparatus 19. The central control apparatus 19 is connected, through a conversion adapter 70, to the endoscopic CCU 10, light source device 11, electric knife apparatus 12, pneumoperitonium 13, VTR 14, display device 16, central display panel 17 and operation panel 18. A voice input/output device 32 in a headset form, for example, is connected to the central control apparatus 19, and each of the appliances can be also controlled by voice.

The central control apparatus 19 has a recording device for recording various kinds of data, such as a hard disk drive (abbreviated to HDD, hereinafter) 19a.

On the other hand, the second trolley includes an endoscopic CCU 20, a light source device 21, an image processing device 22, a display device 23 and a central display panel 24. The endoscopic CCU 20 and light source device 21 are connected to an endoscope 30b.

The display device 23 is a monitor for displaying an endoscopic image, for example. The central display panel 24 is a display unit that can selectively display any data during an operation.

The endoscopic CCU 20, light source device 21 and image processing device 22 are connected to a relay unit 25 included in the second trolley 3. The relay unit 25 is connected to the central control device 19 included in the first trolley 2 via a relay cable 34.

In other words, the central control apparatus 19 can centrally control the endoscopic CCU 10, light source device 11, electric knife apparatus 12, pneumoperitoneum 13, VTR 14, display device 16, central display panel 17 and operation panel 18 included in the first trolley 2 and the endoscopic CCU 20, light source device 21 and image processing device 22 included in the second trolley 3.

The central control apparatus 19 causes the operation panel 18 to display a setting screen for appliance information on the connected appliances and a setting switch. By operating the operation panel 18, operation of each appliance is performed.

A remote controller 31 is mounted to the bed 5 and is an operation device that can be operated by an operating surgeon performing an operation on a patient. The remote controller 31 may be used to operate each appliance through the central control apparatus 19.

The central control apparatus 19 is connected to a patient monitor system 33 and can record biological information obtained from the patient monitor system 33 to the HDD 19a and cause the display device 16 to display data on the recorded biological information such as the pulse and blood pressure.

As described above, one or multiple appliances are connected to the central control apparatus 19 through the conversion adapter 70. The appliance connecting to the central control apparatus 19 is selected based on the circumstances where the medical system 1 is used, such as the type of an operation. The central control apparatus 19 can centrally control and manage appliance information, for example, by communicating with the appliances connected thereto.

Next, the schematic configuration of the communication between the central control apparatus 19 and medical appliances will be described. For simple description, the pneumoperitoneum 13 and VTR 14 are connected to the central control apparatus 19 in the configuration. The description on the configuration that each of the devices normally has, that is, the configuration for performing processing of recording, playing and so on in the VTR 14 will be omitted herein.

Figure 2:
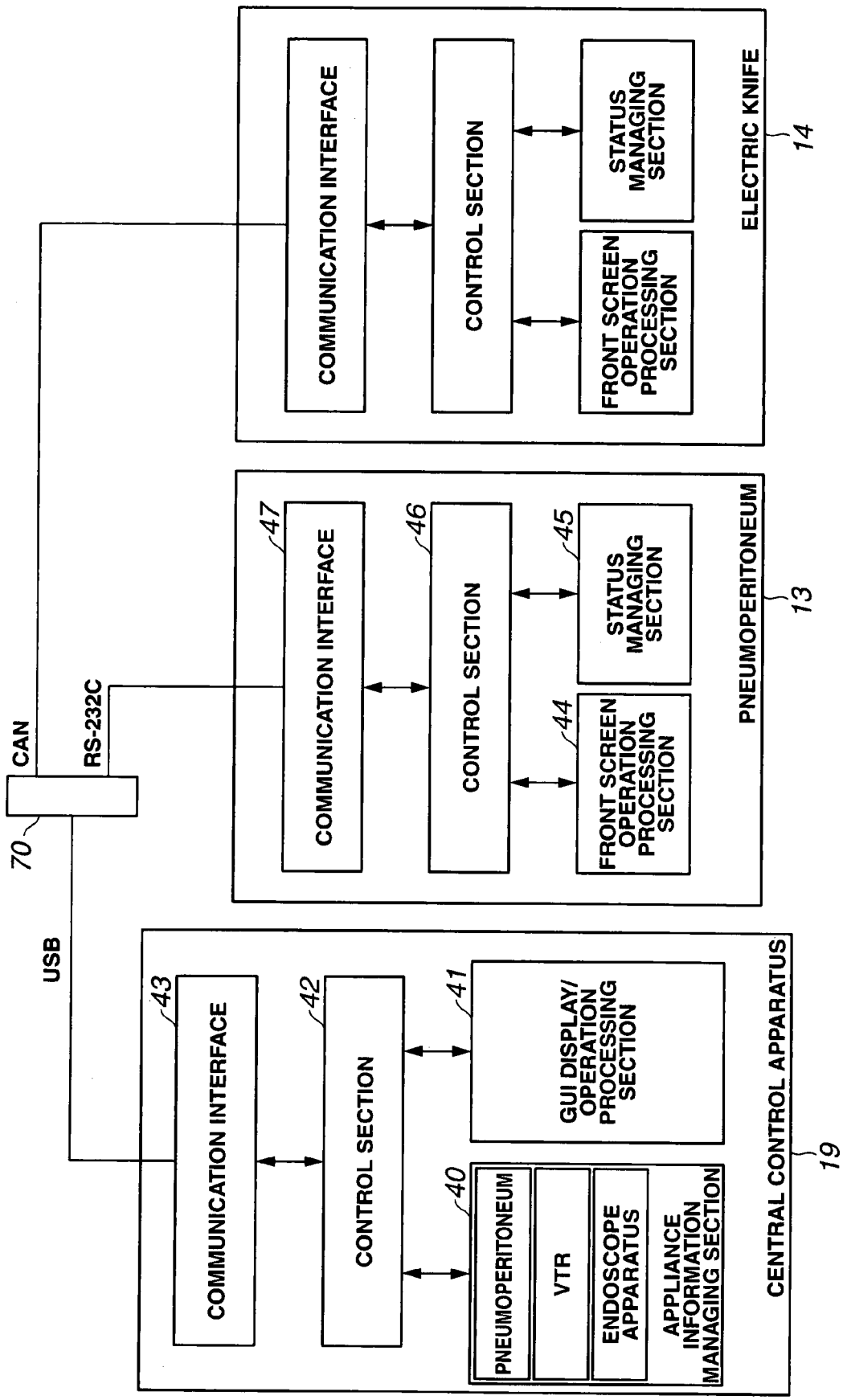
FIG. 2 is a diagram showing schematic configurations of a central control apparatus and medical appliances according to the first embodiment.

FIG. 2 is a diagram showing a schematic configuration between the central control apparatus and medical appliances. As shown in FIG. 2, the central control apparatus 19 includes an appliance information managing section 40, a graphical user interface (abbreviated to GUI, hereinafter) display/operation processing section 41, a control section 42, and a communication interface (abbreviated to communication I/F, hereinafter) 43.

The pneumoperitoneum 13 includes a front screen operation processing section 44, a status managing section 45, a control section 46 and a communication I/F 47. The electric knife 35 has the same configuration as that of the pneumoperitoneum 13.

The control section 42 of the central control apparatus 19 is connected to the appliance information managing section 40, GUI display/operation processing section 41 and communication I/F 43 and controls these sections. The communication I/F 43 is connected to the conversion adapter 70 through a USB, for example.

The control section 46 of the pneumoperitoneum 13 is connected to the front screen operation processing section 44, status managing section 45 and communication I/F 47. The communication I/F 47 may be connected to the conversion adapter 70 through RS-232C, for example.

The electric knife 35 has the same configuration as that of the pneumoperitoneum, and the communication I/F of the electric knife 35 is connected to the conversion adapter 70 through CAN (Controller Area Network: a type of serial communication protocol).

The appliance information managing section 40 of the central control apparatus 19 stores appliance information on the appliances connected thereto. The appliance information may include the output set value and mode of each appliance, for example.

The GUI display/operation processing section 41 performs processing for displaying and operating in an apparatus which accepts inputs, such as the operation panel 18, not shown. The operation panel 18 has a display panel and a touch panel, as described above. The display panel displays appliance information stored in the appliance information managing section 40 and a switch through which an operator can input an operation by using the touch panel. An operator can input an operation by checking the appliance information displayed on the display panel and touching a displayed switch, for example.

When an operation is input, the GUI display/operation processing section 41 outputs an operation signal in accordance with the operation input to the control section 42. The control section 42 transmits communication data in accordance with the operation signal input to the appliance to be operated through the communication I/F 43.

For example, if the appliance to be operated is the pneumoperitoneum 13, the communication data based on USB is converted to the communication data based on RS-232C by the conversion adapter 70 and is transmitted to the communication I/F 47 of the pneumoperitoneum 13. Details of the processing on communication data in the conversion adapter 70 will be described later.

In the pneumoperitoneum 13, the communication data received through the communication I/F 47 is input to the control section 46. The control section 46 controls operations of the sections of the pneumoperitoneum 13 according to the content of the inputted communication data.

The front screen operation processing section 44 of the pneumoperitoneum 13 has an operation unit, not shown, and an operator can operate the pneumoperitoneum 13 by using the operation unit. The front screen operation processing section 44 outputs the control signal to the control section 46 thereto when an operation is input through the operation unit. The control section 46 controls an operation of each section of the electric knife 35a manufactured by A in accordance with an input operation signal.

When the pneumoperitoneum 13 is thus operated, the appliance information of the pneumoperitoneum 13 changes. The status managing section 45 stores the appliance information of the pneumoperitoneum 13, and the stored appliance information is constantly updated to the latest appliance information by the control section 46. The appliance information is also reflected to the display by a display unit, not shown, connecting to the front screen operation processing section 44.

The change in appliance information is also reflected to the display by the operation panel 18 connecting to the GUI display/operation processing section 41 of the central control apparatus 19. When the appliance information of the pneumoperitoneum 13 changes, the control section 46 transmits an update command for updating appliance information stored in the central control apparatus 19 as communication data to the central control apparatus 19.

The transmitted communication data is transmitted to the communication I/F 43 of the central control apparatus 19 through the conversion adapter 70. Upon receipt of the communication data, the control section 42 updates the appliance information of the pneumoperitoneum 13, which is stored in the appliance information managing section 40. The updated appliance information is reflected to the display by the operation panel 18 connecting to the GUI display/operation processing section 41.

Having described the communication between the central control apparatus 19 and the pneumoperitoneum 13, the same configuration and operations are performed also in the communication between the central control apparatus 19 and the other apparatuses including the electric knife 35.

In this way, the central control apparatus 19 exchanges communication data with an apparatus connecting thereto. The communication data includes data signals "1" and "0". The appliances connecting to the central control apparatus 19 may differently interpret what kind of communication data the communication data signals are. In other words, the meaning of communication data obtained from data signals may depend on the appliance that receives the communication data.

Figure 3:
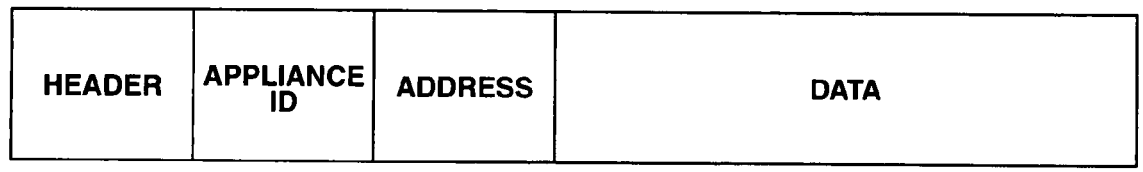
FIG. 3 is a diagram showing an example of the configuration of communication data to be communicated between the central control apparatus and medical appliances.

The interpretation of the data signals, that is, the definition of the communication data (called command definition, hereinafter), which is function information, will be described below. FIG. 3 is an example of the configuration of communication data to be communicated between the central control apparatus and a medical appliance. As shown in FIG. 3, communication data includes a header, an appliance ID and a category ID, an address, data and ACK/NAK (not shown).

The header is a part indicating the details of communication data and may include information on the sender, receiver and length indicating the data length of the communication data. The appliance ID is a part indicating the appliance that the communication data is for. The address is a part indicating a function of the appliance. The data is a part indicating how the function specified by the address is to be controlled. Apparently, ACK/NAK is a part indicating the communication data is either positive response or negative response.

For example, in data signals transmitted from the central control apparatus 19, the output of an electric knife is set at 10 W where the appliance ID having the value "1000" refers to an electric knife, the address having the value "0101" refers to the output set value, and the data having the value "1010" refers to 10 W.

In other words, the command definition may include the value of an appliance ID, the value of an address and the values of data referring to the types of appliance and function and determines the rule for controlling the appliance and function.

As described above, since each appliance connecting to the central control apparatus 19 has a different command definition, the central control apparatus 19 needs exchanging communication data based on the command definition of the appliance to be operated. Having described the present embodiment under the concepts of the address and function, function commands may be adopted that are for operations in response to A1 and A2 only, which are general function commands (A1: Function 1, A2: Function 2 and so on), for example.

Accordingly, in the medical system 1 according to the present embodiment, the appliances having a common function are categorized and have a common command definition for each category. Thus, the communication between the central control apparatus 19 and an appliance can be performed efficiently. For example, it is assumed that an electric knife manufactured by A, an ultrasonic knife manufactured by A and an electric knife manufactured by B belong to a category "Electric Knife" and that a camera manufactured by A and a camera, digital recorder and printer manufactured by B belong to a category "Camera". In the category "Electric Knife", the functions such as output-value setting and mode switching are common functions.

Details of the communication employing a common command according to the present embodiment will be described below. For simple description, the central control apparatus 19 is connected to an appliance belonging to the category "Electric Knife" here. The same configuration and operations are implemented for appliances connecting to the central control apparatus 19, which belong to the other categories excluding the category "Electric Knife".

Figure 4:
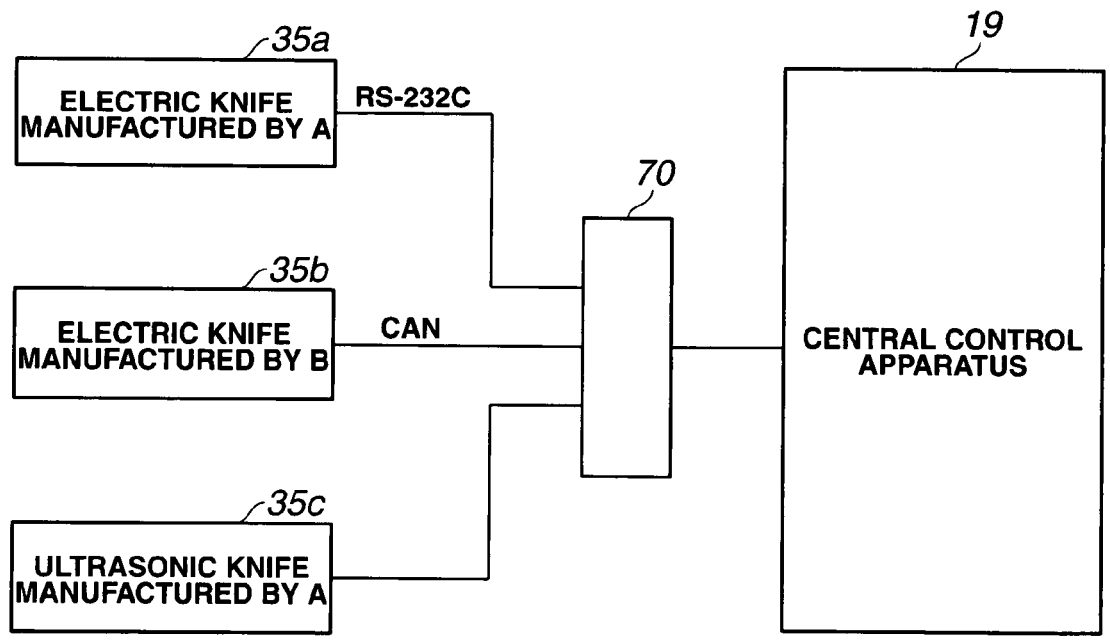
FIG. 4 is a diagram showing medical appliances belonging to the category of "electric knife"

FIG. 4 is a diagram showing medical appliances belonging to the category "Electric Knife". The central control apparatus 19 as shown in FIG. 4 is connected to the electric knife 35a manufactured by A, the electric knife 35b manufactured by B and the ultrasonic knife 35c manufactured by A. The electric knife 35a manufactured by A, the electric knife 35b manufactured by B and the ultrasonic knife 35c manufactured by A have different interfaces and protocols. For example, the electric knife 35a manufactured by A is connected to the central control apparatus 19 by RS-232C. The electric knife 35b manufactured by B is connected to the central control apparatus 19 by CAN.

Figure 5:
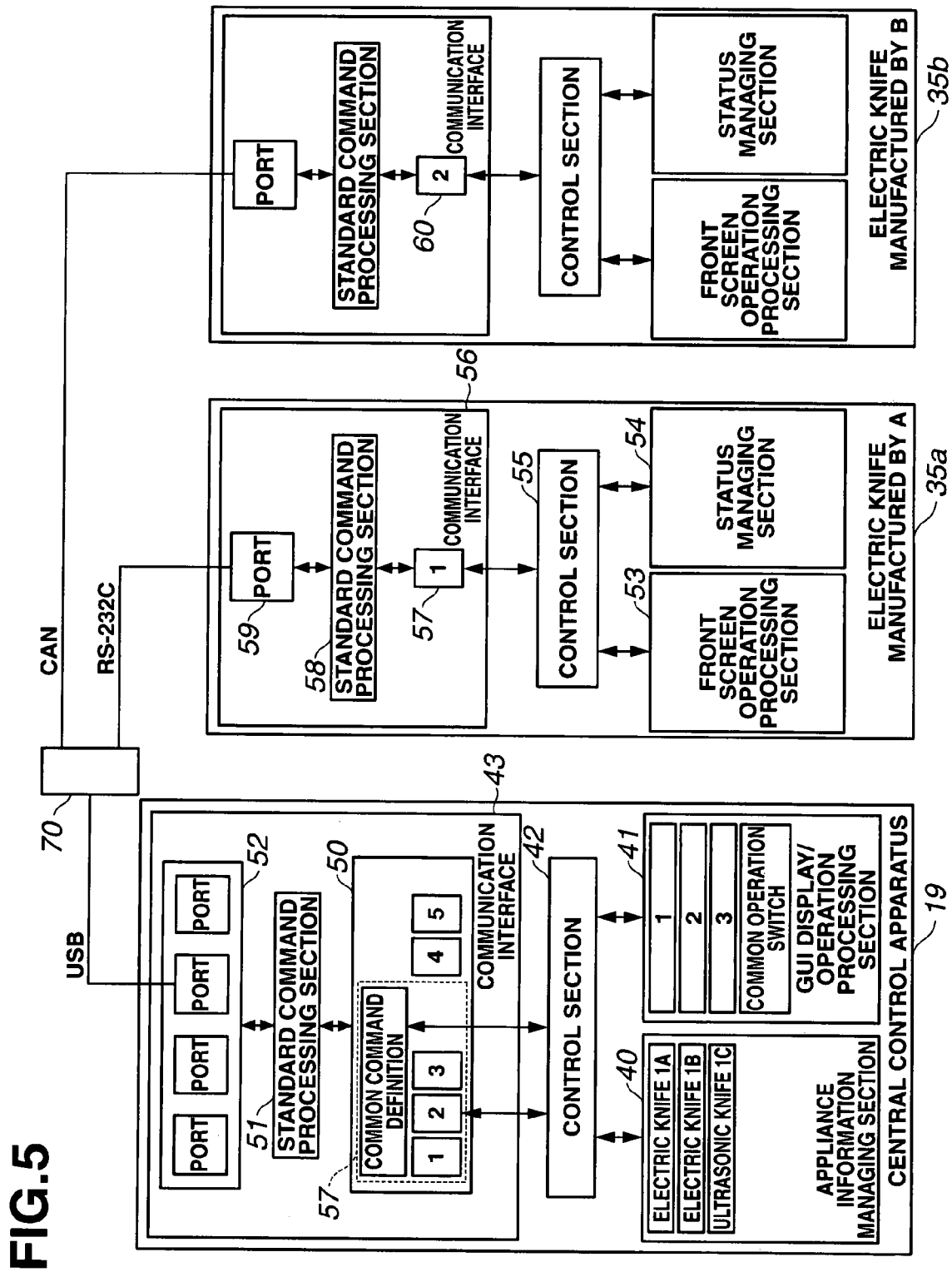
FIG. 5 is a schematic configuration diagram of the central control apparatus and medical appliances belonging to the category of "electric knife" according to the first embodiment.

Next, FIG. 5 shows schematic configurations of the central control apparatus, electric knife manufactured by A and electric knife manufactured by B. For simple description, the description on the ultrasonic knife 35c manufactured by A will be omitted herein. The same reference numerals are given to the same components of the central control apparatus 19 as those in FIG. 2, and the description will be omitted herein.

As shown in FIG. 5, the communication I/F 43 of the central control apparatus 19 includes an appliance-specific command interpreting section 50, a standard command processing section 51 and a port 52.

The electric knife 35a manufactured by A includes a front screen operation processing section 53, a status managing section 54, a control section 55 and a communication I/F 56. The communication I/F 56 includes a command interpreting section 57 and a standard command processing section 58 and a port 59.

The electric knife 35b manufactured by B has the same configuration as that of the electric knife 35a manufactured by A except that the communication I/F includes a command interpreting section 60 instead of the command interpreting section 57.

The appliance-specific command interpreting section 50 of the central control apparatus 19 stores a command definition (called common command definition hereinafter) for a common function in the category "Electric Knife" as common function information and a command function (called unique command definition) for a unique function of each appliance excluding the common function as unique function information. FIG. 5 shows unique command definitions as DEFINITIONS 1, 2, 3, 4 and 5. For example, DEFINITION 1 is a unique command definition for the electric knife 35a manufactured by A, and DEFINITION 2 is a unique command definition for the electric knife 35b manufactured by B. The details of the command definitions will be described later.

The command interpreting section 57 of the electric knife 35a manufactured by A stores DEFINITION 1 of the electric knife 35a manufactured by A only, and the command interpreting section 60 of the electric knife 35b manufactured by B stores DEFINITION 2 of the electric knife 35b manufactured by B only.

Each of the central control apparatus 19, electric knife 35a manufactured by A and electric knife 35b manufactured by B includes a standard command processing section. The standard command processing section adds the header and data signals such as ACK/NAK to communication data, for example.

The central control apparatus 19 interprets data signals based on the common command definition in the category "Electric Knife" and the unique command definition for a unique function of each appliance when the central control apparatus 19 receives the communication data from an appliance under the category "Electric Knife". For example, the communication data received from the electric knife 35a manufactured by A is interpreted based on the common command definition and the unique command definition 1. The communication data interpreted from the data signals is input to the control section 42.

The control section 42 controls the applicable components of the central control apparatus 19 based on the input communication data.

The GUI display/operation processing section 41 causes the operation panel 18 to display the appliance information and operation switch for a common function of categories.

Details of the common command definition and unique command definition will be described below. First of all, FIG. 6 shows a table example of the command definitions.

As shown in FIG. 6, the table of command definitions includes higher data, lengths, lower data, reservation parts, addresses to display, display types and operation types.

The higher data is a part corresponding to the address in FIG. 3 and is a data part indicating the function. The higher data includes data signals of a fixed length of one byte, for example. In order to add the command definition indicating a function of each appliance, the higher data may be added.

The length is a data part indicating the length of valid data of the reservation part, which will be described later.

The lower data is a part corresponding to the data in FIG. 3 and is a data part indicating the type of control to be implemented over the function indicated by the higher data. The lower data includes data signals of a fixed length of 2 bytes, for example.

The reservation part is a data part of a variable length to be used for extending lower data, and the length of the valid data is defined by the length. For example, when the higher data is "select mode" in communication data and when the appliance applicable to the communication data has two kinds of modes, all modes can be expressed by the lower data of a fixed length. However, when the appliance has 1000 kinds of modes, for example, all of the modes may not be expressed by lower data of a fixed length only. Thus, the reservation part is used to express all of the modes.

On the table of command definitions shown in FIG. 6, the common command definition is the part 65 including the higher data, length and lower data. The unique command definition includes the reservation part 66, which is a data extension part, and a row on which the upper data is "add new function" in FIG. 6, which is the function extension part 67.

The use of the definition having the reservation part of a variable length allows the easier extension of lower data of the function expressed by the upper data. When a new appliance belonging to the same category is connected to the central control apparatus 19 to use, the new appliance becomes compatible only by adding the function extension part 67 of the upper data without changing the common command definition 65. As a result, the burden on the development of the central control apparatus 19 can be reduced.

Display and operation types are included in a display/operation method definition part 68.

The display type is a data part that defines the display of the output set value in steps of either one or five, for example. The operation type is a data part defining an operation method such as "hold button" and "toggle", for example. These display position address, display type and operation type are used for allocation, which will be described later. Details of the allocation will be described later.

Next, specific examples of the functions of the appliances, which are defined in this way, will be described. FIG. 7 is a diagram showing examples of the functions under the category "Electric Knife". As shown in FIG. 7, in the case of the function "select mode", the electric knife 35*a* manufactured by A has two modes of bi-polar and mono-polar. The electric knife 35*b* manufactured by B has only a bi-polar mode. The ultrasonic knife 35*c* manufactured by A has two modes of normal mode and special mode.

In the case of a function "output value setting: A", the electric knife 35*a* manufactured by A is defined to the step of one from zero to 400 W. The electric knife 35*b* manufactured by B is defined to the steps of five from zero to 200 W. The ultrasonic knife 35*c* manufactured by A is defined to the steps of ten from zero to 100 W.

In the case of a function "output value setting: B", the electric knife 35*a* manufactured by A is defined to the step of one from zero to 200 W. The electric knife 35*b* manufactured by B is defined to the steps of five from zero to 100 W. The ultrasonic knife 35*c* manufactured by A is defined to the steps of ten from zero to 100 W.

In the case of a function "output value setting: C", the electric knife 35*a* manufactured by A is defined to the step of one from zero to 500 W. The electric knife 35*b* manufactured by B is defined to the step of one from zero to 600 W. The ultrasonic knife 35*c* manufactured by A does not have the function of the output value setting: C.

In the case of a function "output value setting: D", the electric knife 35*a* manufactured by A is defined to the step of one from zero to 500 W. The electric knife 35*b* manufactured by B and the ultrasonic knife 35*c* manufactured by A do not have the function of the output value setting: D.

In the case of a function "special mode", the electric knife 35*a* manufactured by A has two modes of "normal mode" and "test mode". The electric knife 35*b* manufactured by B does not have a function "add special mode". The ultrasonic knife 35*c* manufactured by A has two modes of "normal mode" and "test mode".

In the case of a function "switch output destination", the electric knife 35*a* manufactured by A can switch the on/off of a remote switch. The electric knife 35*b* manufactured by B does not have a function "switch output destination". The ultrasonic knife 35*c* manufactured by A can switch the output of a foot switch in accordance with the pattern 1→2→3→4.

The table showing functions for each appliance is called appliance-specific function table. On the appliance-specific function table under the category "Electric Knife", the "select mode", "output value setting: B", "output value setting: C" and "output value setting: D" are common functions under the category "Electric Knife". On the other hand, the "special mode" and "switch output destination" are unique functions to the appliances.

Figure 8:
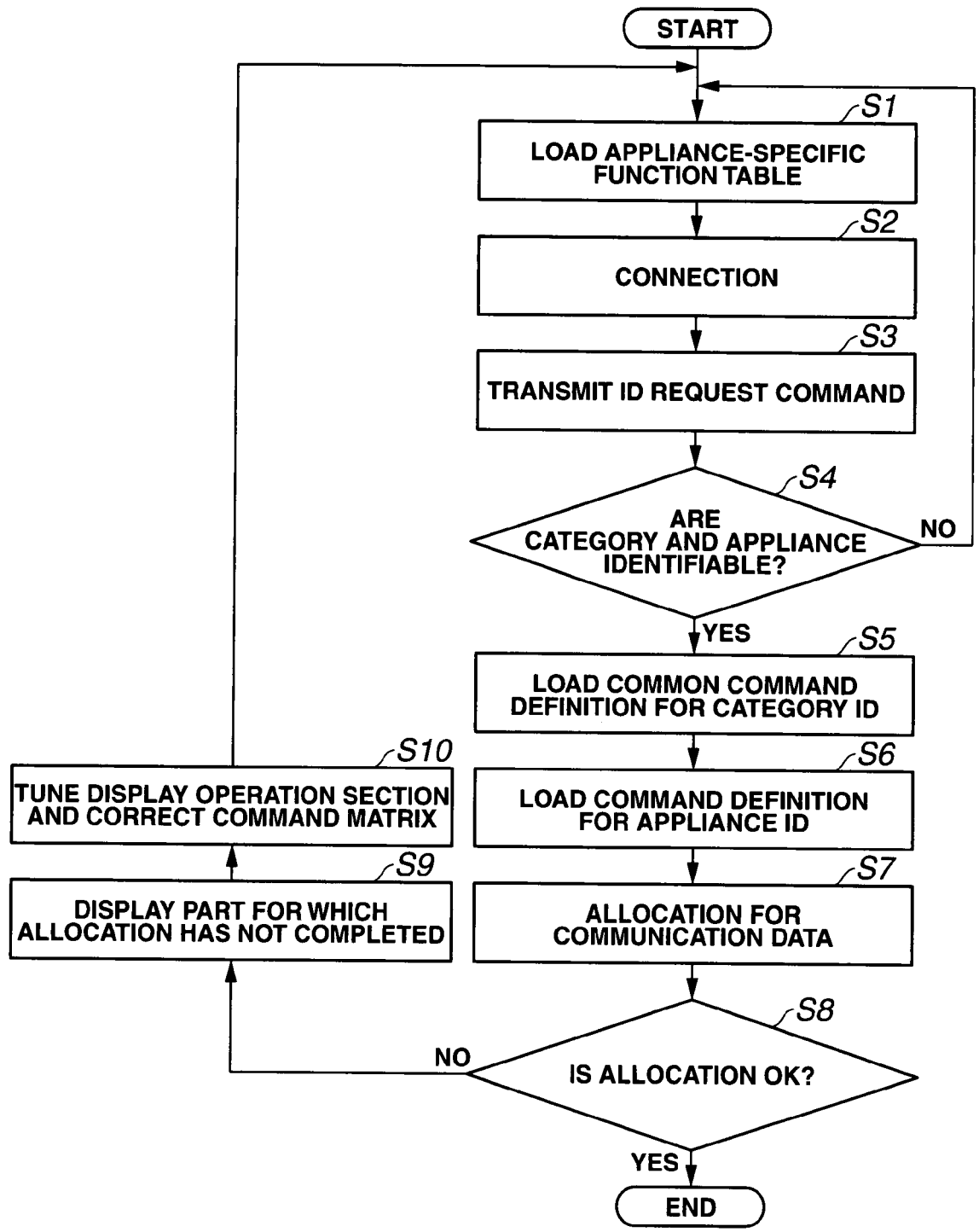
FIG. 8 is a flowchart showing an example of the step flow of communication assignment according to the first embodiment.

The central control apparatus 19 in this configuration must perform communication allocation processing when an appliance is connected thereto to use first. Steps of the communication allocation processing will be described below. FIG. 8 is a flowchart showing an example of the flow of steps of the communication allocation processing.

First, an operator causes the central control apparatus 19 to load the appliance-specific function table (step S1). The appliance-specific table is created in advance by using another appliance such as a personal computer (abbreviated to PC, hereinafter).

Then, the operator connects an appliance such as the electric knife 35*a* manufactured by A, for example, to the central control apparatus 19 (step S2).

Next, the operator causes the central control apparatus 19 to transmit an ID request command to the connected appliance (step S3). The ID request command is a command that requests the central control apparatus 19 to transmit the appliance ID and category ID of the connected appliance.

Next, the operator determines whether the control section 42 has been able to identify the appliance ID and category ID of the connected appliance or not (step S4). If the appliance ID and category ID of the connected appliance have been identified, the processing moves to step S4. If the appliance ID and category ID of the connected appliance have not been identified, for example, if the appliance ID and category ID may not have been received from the connected appliance, the processing moves to step S1 and the processing is repeated.

Then, the operator causes the central control apparatus 19 to load the common command definition corresponding to the category ID of the connected appliance (step S5).

Next, the operator causes the central control apparatus 19 to load the unique command definition corresponding to the appliance ID of the connected appliance (step S6).

Then, the operator causes the central control apparatus 19 to perform allocation (step S7). The allocation is performed for determining which appliance information is to be displayed and which operation switch is to be displayed on a display unit such as the operation panel 18 based on the display/operation method definition part 68.

Then, the operator determines whether the allocation has been completed or not (step S8). In other words, the operator determines whether the allocation has been completed without errors. If the allocation has not been completed, the processing moves to step S9. If the allocation has been completed, the communication assignment processing ends.

If the allocation has not been completed, the operator causes the display unit such as the operation panel 18 to display the command definition part for which the allocation has not been completed (step S9).

Then, the operator corrects the part for which the allocation has not been completed, which is displayed in step S9 (step S10). After that, the processing moves to step S1 again, and the communication assignment processing is repeated. Thus, the central control apparatus 19 recognizes the functions of the connected appliance, and the operator can allocate command buttons in a preferred order and at preferred positions by using the GUI of the operation panel 18.

When the allocation processing on the screen ends, the appliance connected to the central control apparatus 19 is available to the operator. The screen allocation processing may be performed by a PC or the control section 42 through a program instead of the operator. Furthermore, information may be pre-stored in each appliance connecting to the central control apparatus 19. Thus, the allocation processing as shown in FIG. 8 is not required.

Figure 9:
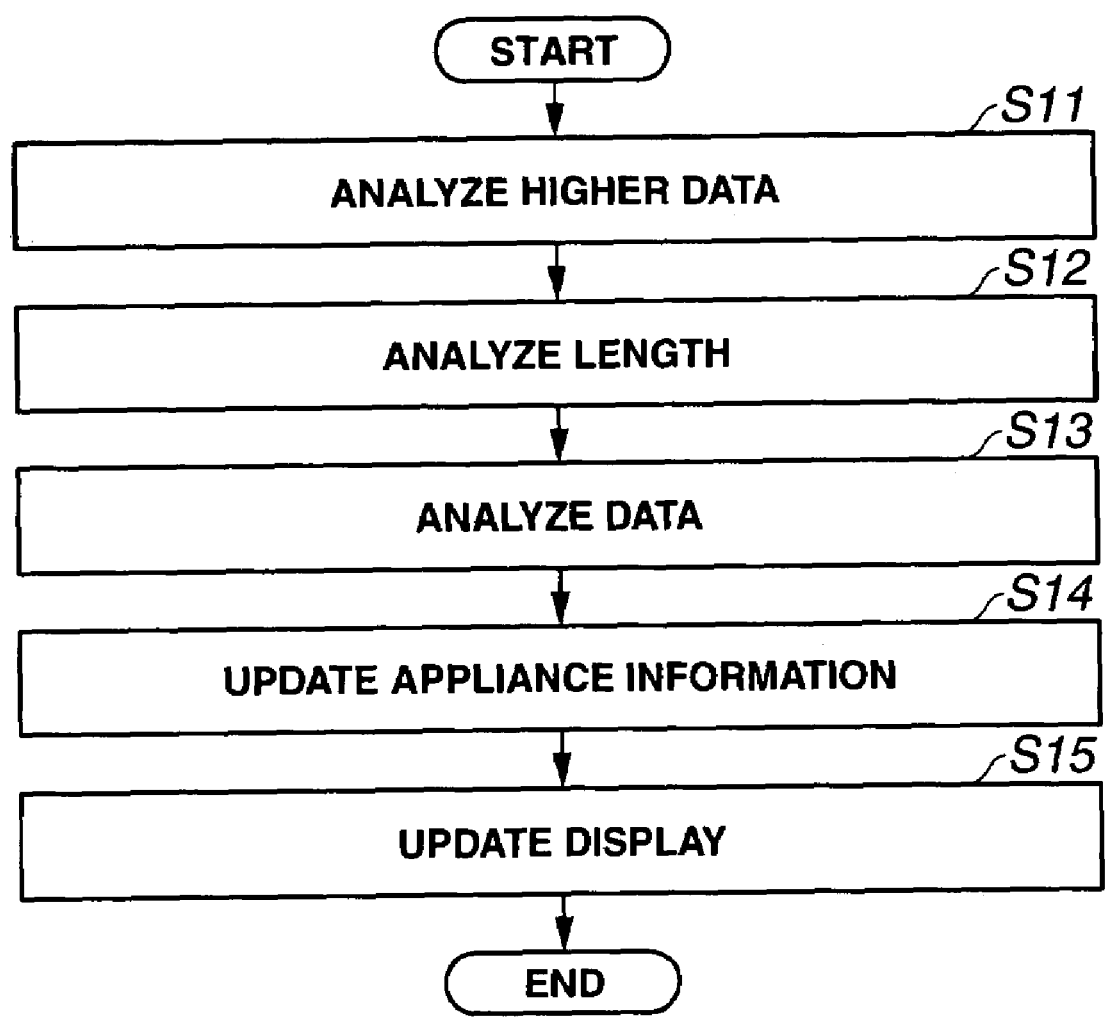
FIG. 9 is a flowchart showing an example of the processing flow when communication data is received from a connected device according to the first embodiment.
Figure 10:
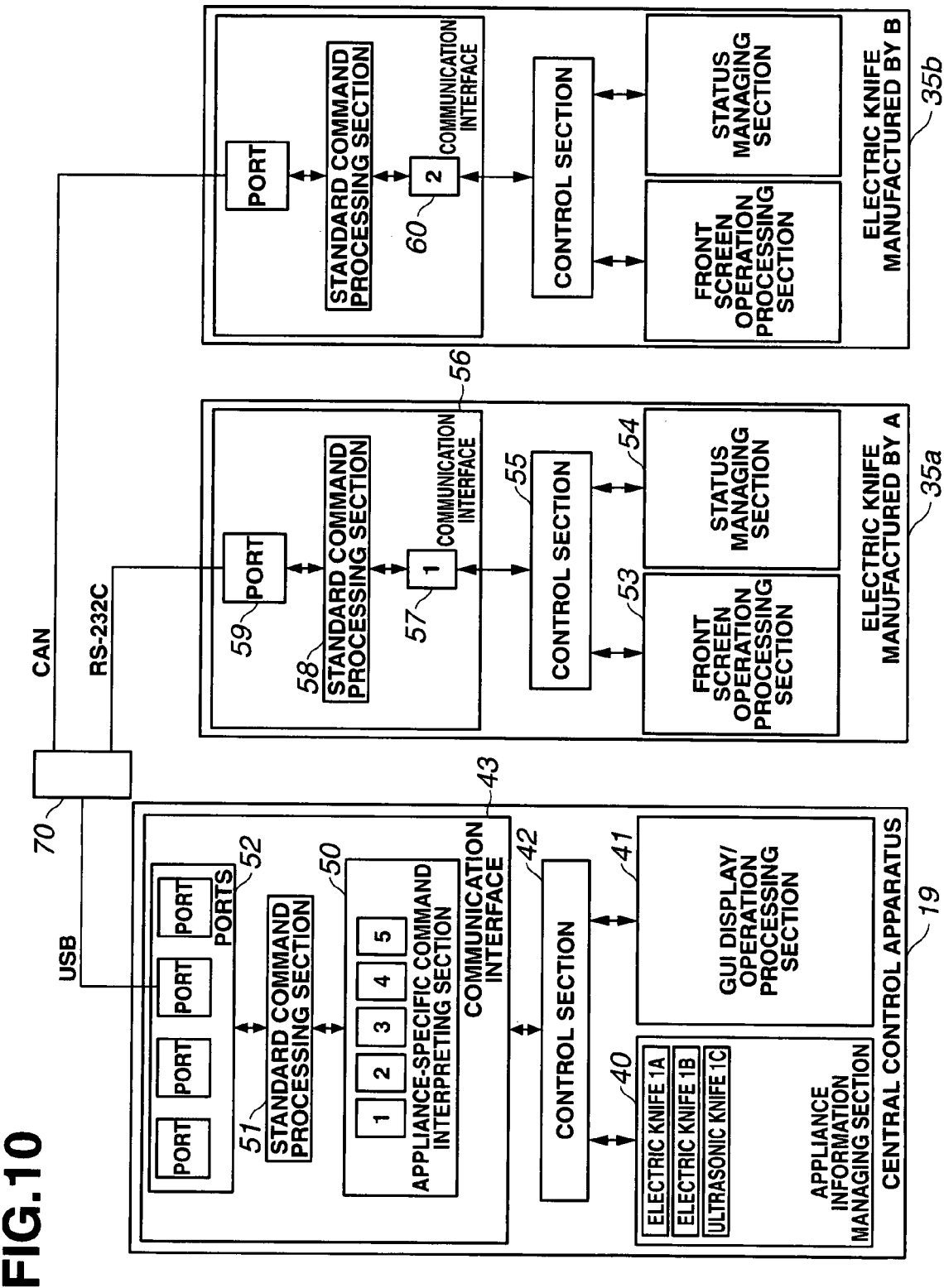
FIG. 10 is a diagram showing a schematic configuration of the central control apparatus with no common command definitions according to the first embodiment.

Next, the processing will be described which is to be performed if the central control apparatus 19 receives communication data from a connected appliance after the completion of the communication allocation. FIG. 9 is a flowchart showing an example of the flow of processing to be performed when communication data is received from a connected appliance. The processing starts when the central control apparatus 19 receives communication data from an appliance connected thereto.

First, the control section 42 causes the appliance-specific command interpreting section 50 to analyze higher data of the received communication data (step S11).

Then, the control section 42 causes the appliance-specific command interpreting section 50 to analyze the length of the received communication data (step S12).

Next, the control section 42 causes the appliance-specific command interpreting section 50 to analyze the data based on the loaded length (step S13). In other words, step S13 analyzes the lower data and reservation part.

The control section 42 also updates the appliance information of the appliance information managing section 40 based on the communication data analyzed in steps S11 through step S13 (step S14).

Then, the control section 42 causes the GUI display/operation processing section 41 to update the display of the display unit such as the operation panel 18 based on the updated appliance information (step S15).

Then, the processing ends, and the processing is repeated in response to the receipt of the communication data subsequently.

As described above, when communication data is received, the appliance-specific command interpreting section 50 analyzes the communication data based on the common command definitions and unique command definitions.

Now, details of the processing on communication data in the conversion adapter 70 according to the present embodiment will be described. The conversion adapter 70 allows efficient communication between the central control apparatus 19 and various appliances, which have different protocols and interfaces, by connecting the central control apparatus 19 and the various appliances.

Figure 11:
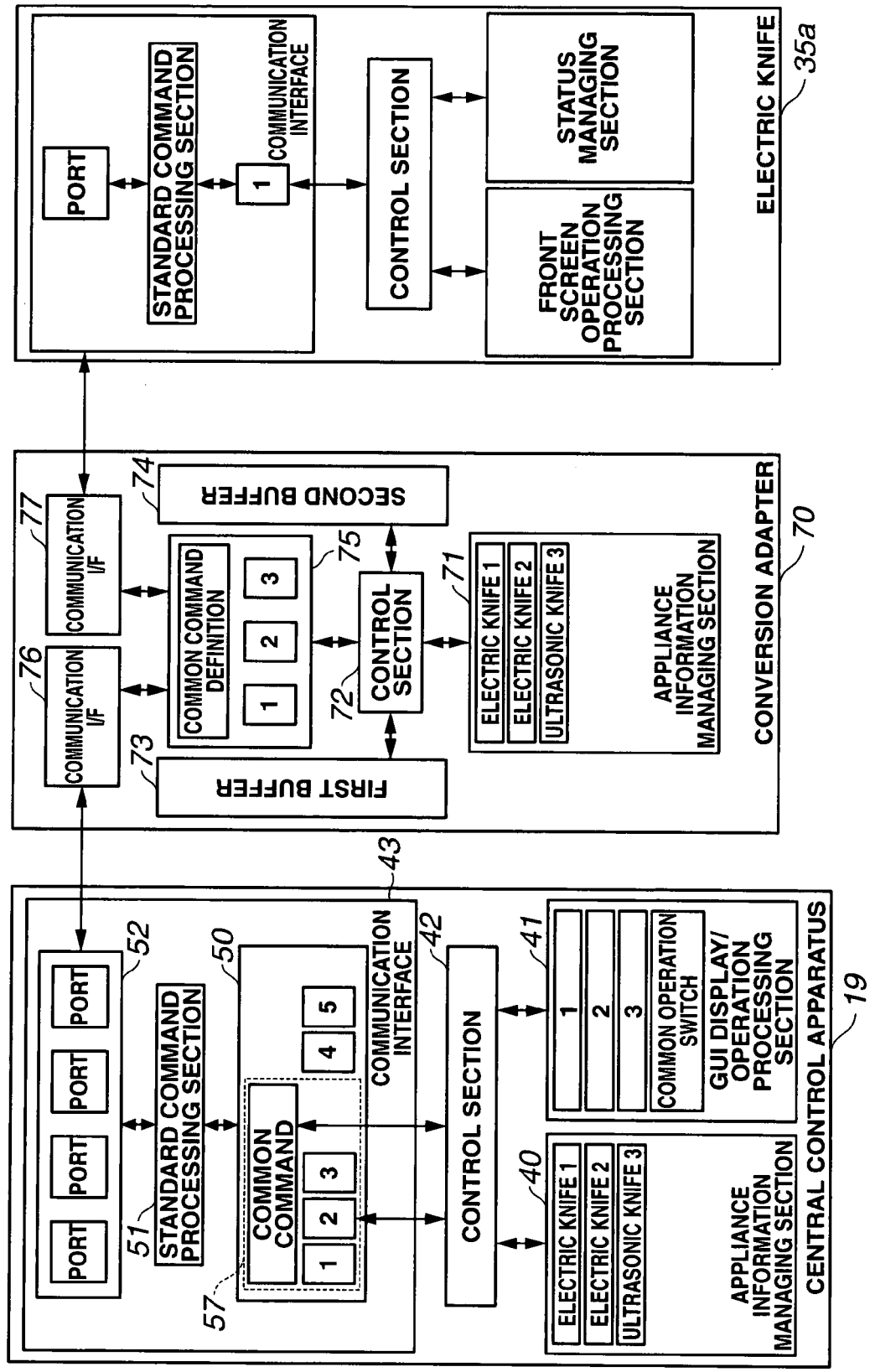
FIG. 11 is a schematic configuration diagram of a conversion adapter according to the first embodiment.

A schematic configuration of the conversion adapter 70 will be described below. FIG. 11 is a schematic configuration diagram of the conversion adapter. In the description below, the central control apparatus 19 and the electric knife 35a manufactured by A belonging to the category "Electric Knife" are only connected to the conversion adapter 70. The same reference numerals are given to the same components as those in FIGS. 2 and 5, and the description will be omitted herein.

As shown in FIG. 11, the conversion adapter 70 includes an appliance information managing section 71, a control section 72, a first buffer 73 functioning as a first storage unit, a second buffer 74 functioning as a second storage unit, an appliance-specific command interpreting section 75 functioning as a data extracting unit, a communication I/F 76 functioning as a first communication unit, and a communication I/F 77 functioning as a second communication unit.

The control section 72 includes a CPU and is connected to the appliance information managing section 71, first buffer 73, second buffer 74 and appliance-specific command interpreting section 75. The appliance-specific command interpreting section 75 is connected to the communication I/F 76 and communication I/F 77. The control section 72 controls operations of the components within the conversion adapter 70.

The communication I/F 76 is connected to the central control apparatus 19. The connection is performed through USB at a communication speed of 12 Mbps, for example. The communication I/F 76 exchanges data signals with the central control apparatus 19 based on a communication protocol (called first protocol, hereinafter) with the conversion adapter 70.

The communication I/F 77 is connected to the electric knife 35a manufactured by A. The connection is performed through RS-232C at a communication speed of 9600 bps, for example. The communication I/F 77 exchanges data signals with the electric knife 35a manufactured by A based on a communication protocol (called second protocol hereinafter) with the conversion adapter 70.

The data signals received by the communication I/F 76 and communication I/F 77 are input to the appliance-specific command interpreting section 75. The appliance-specific command interpreting section 75 has the same configuration as that of the appliance-specific command interpreting section 50 in the central control apparatus 19. In other words, the appliance-specific command interpreting section 75 stores a common command definition for a common function to appliances under the category "Electric knife" as a common function table and a unique command definition for a unique function to each appliance as a unique function table. The appliance-specific command interpreting section 75 interprets the received data signals based on the common command definition and unique command definition, and the interpreted communication data is transmitted to an applicable component by the control section 72, and various processing is performed thereon.

The first buffer 73 stores the communication data received through the communication I/F 76 and the connection information of an appliance connected through communication. When the data amount of the communication data stored in the first buffer 73 is higher than a predetermined data amount, the stored oldest data is sequentially deleted. A predetermined amount of new communication data is always stored in the first buffer 73. Alternatively, an error due to "buffer-full" may be given.

On the other hand, the second buffer 74 stores communication data received through the communication I/F 77 and appliance information of an appliance connected thereto through communication. When the data amount of the communication data stored in the second buffer 74 is higher than a predetermined data amount, the stored oldest data is sequentially deleted. A predetermined amount of new communication data is always stored in the second buffer 74. The stored communication data is read out at a predetermined time based on the first protocol and is transmitted to the central control apparatus 19 through the communication I/F 76.

The appliance information managing section 71 stores appliance information of an appliance connecting to the conversion adapter 70 like the appliance information managing section 40 of the central control apparatus 19. The appliance information managing section 71 stores latest appliance information.

The control section 72 compares the appliance information stored in the appliance information managing section 71 and the appliance information expressed by the communication data stored in the first buffer 73. When the appliance information stored in the appliance information managing section 71 gets older, communication data expressing the latest appliance information stored in the first buffer 73 is stored in the appliance information managing section 71.

The communication data expressing the stored latest appliance information is read out at a predetermined time based on the second protocol and is transmitted to the electric knife 35*a* manufactured by A through the communication I/F 77. When the control section 72 receives predetermined communication data such as command data from the electric knife 35*a* manufactured by A through the communication I/F 77, the control section 72 transmits a response signal to the electric knife 35*a* manufactured by A.

As described above, the protocol between the conversion adapter 70 and the central control apparatus 19 is different from the protocol between the conversion adapter 70 and the electric knife 35*a* manufactured by A.

Therefore, when communication data is transmitted from the central control apparatus 19 to the electric knife 35*a* manufactured by A, for example, the control section 72 causes the first buffer 73 to store the received communication data and transmits the received communication data to the electric knife 35*a* manufactured by A at the timing based on the second protocol.

Conversely, when communication data is transmitted from the electric knife 35*a* manufactured by A to the central control apparatus 19, the control section 72 causes the second buffer 74 to store the received communication data and transmits the received communication data to the central control apparatus 19 at the timing based on the first protocol.

Performing this processing can absorb the difference in communication speed and/or difference in data format between the first protocol and the second protocol, which can prevent unnecessary communication and can increase the efficiency of the communication.

In the same manner, transmitting a response signal by the conversion adapter 70 in response to the receipt of communication data can eliminate waste in the communication due to a difference in communication speed between the first protocol and the second protocol. In other words, when predetermined communication data such as command data is transmitted from the electric knife 35*a* manufactured by A, for example, a time lag occurs before the electric knife 35*a* manufactured by A receives the response signal from the central control apparatus 19, which decreases the efficiency of communication.

An operation by the conversion adapter 70 in this configuration will be described below.

Figure 12:
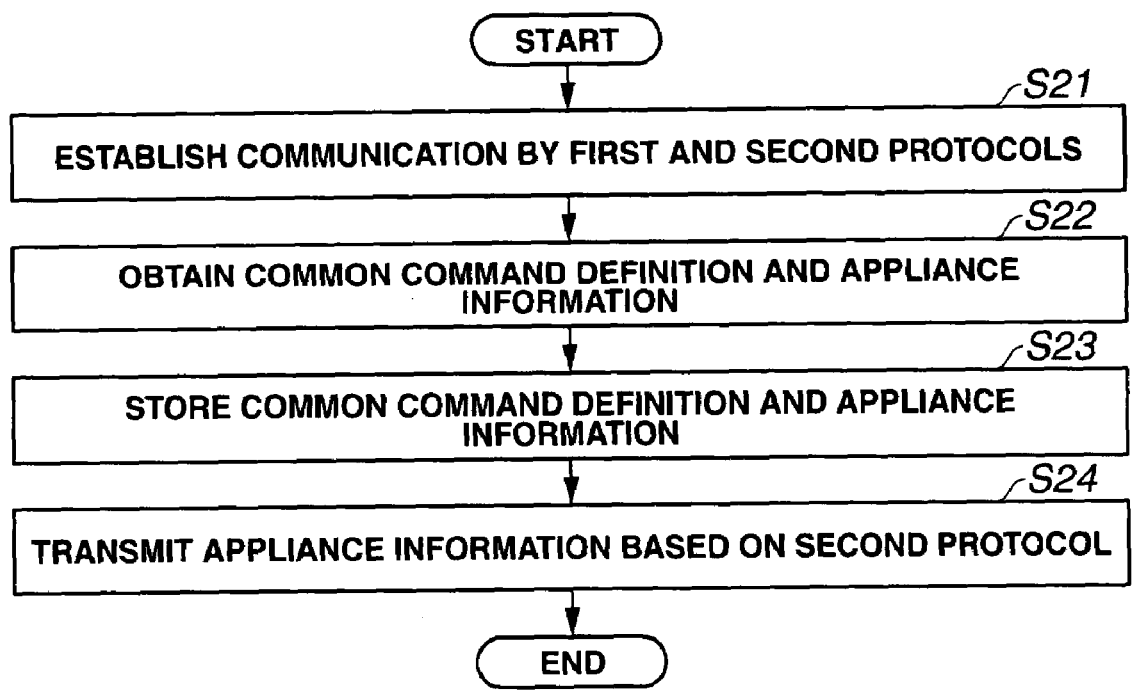
FIG. 12 is a flowchart showing an example of the flow of processing of setting a conversion adapter according to the first embodiment.

Referring to FIG. 12, setting processing to be performed first when the conversion adapter 70 is connected to the central control apparatus 19 and the electric knife 35*a* manufactured by A will be described below. FIG. 12 is a flowchart showing an example of the setting processing flow in the conversion adapter.

It is assumed that the setting processing starts when the conversion adapter 70 is connected to the central control apparatus 19 and the electric knife 35*a* manufactured by A.

First, the control section 72 establishes communication by the first and second protocols (step S21). In other words, the communication between the conversion adapter 70 and the central control apparatus 19 is thus allowed, and the communication between the conversion adapter 70 and the electric knife 35*a* manufactured by A is thus allowed.

Then, the control section 72 obtains a common command definition and appliance information by the first protocol (step S22). At this step, the common command definition stored by the central control apparatus 19 and the appliance information of the each appliance are obtained.

Then, the control section 72 has the common command definition and appliance information stored (step S23). The control section 72 causes the appliance-specific command interpreting section 75 and appliance information managing section 71 to store the common command definition and appliance information, respectively.

Next, the control section 72 transmits the appliance information to the electric knife 35*a* manufactured by A based on the second protocol (step S24). In this step, the electric knife 35*a* manufactured by A stores the initial set value, which is the appliance information.

Then, the setting processing in the conversion adapter 70 ends.

Figure 13:
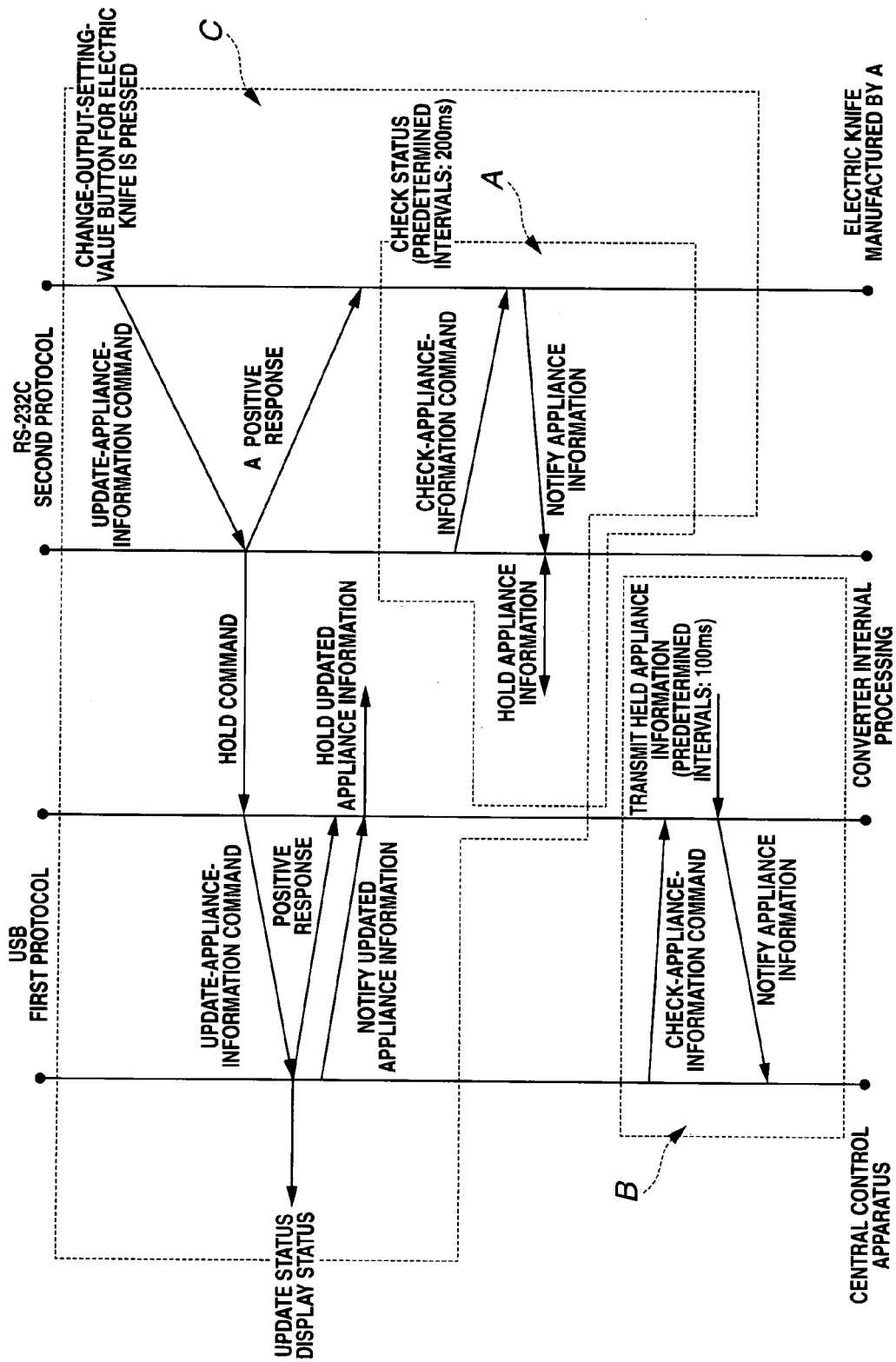
FIG. 13 is a timing chart showing an example of the flow in the communication among the central control apparatus, the conversion adapter and an electric knife manufactured by A.

When the setting processing in the conversion adapter 70 ends, communication between appliances is performed. Details of the communication will be described below. FIG. 13 is a timing chart in the communication among the central control apparatus, conversion adapter and electric knife manufactured by A.

First, the conversion adapter 70 performs processing called periodical polling (indicated by A in FIG. 13) at a predetermined time intervals in order to eliminate the difference between the current appliance information of the electric knife 35*a* manufactured by A and the electric knife 35*a* manufactured by A stored in the central control apparatus 19. The interval of the periodical polling is defined by the second protocol, and the conversion adapter 70 transmits a check-appliance-information command to the electric knife 35*a* manufactured by A every 200 ms, for example.

The check-appliance-information command transmitted from the conversion adapter 70 is received by the electric knife 35*a* manufactured by A. The electric knife 35*a* manufactured by A returns the latest value to the conversion adapter 70 in response to the receipt of the check-appliance-information command. The conversion adapter 70 stores it in the second buffer.

On the other hand, the central control apparatus 19 also performs the periodical polling (indicated by B in FIG. 13) as an appliance data updating step in order to eliminate the difference between the appliance information of the electric knife 35*a* manufactured by A stored in the conversion adapter 70 and the appliance information of the electric knife 35*a* manufactured by A stored in the central control apparatus 19. The interval of the periodical polling is defined by the first protocol, and the central control apparatus 19 transmits the check-appliance-information command stored in the second buffer to the conversion adapter 70 every 100 ms, for example.

In response to the receipt of the check-appliance-information command, the conversion adapter 70 transmits the appliance information of electric knife 35*a* manufactured by A stored in the appliance information managing section 71 to the central control apparatus 19. The central control apparatus 19 stores the received appliance information of the electric knife 35*a* manufactured by A in the appliance information managing section 40.

The first buffer 73 and second buffer 74 include a transmit buffer and a receive buffer, not shown, and temporarily hold the values bi-directionally exchanged through the communication I/Fs 76 and 77 and cause the appliance information managing section 71 to update the values at a predetermined timing of the control section 72.

In this way, the central control apparatus 19 and conversion adapter 70 perform the periodical polling so that the each apparatus can always share the latest appliance information.

Here, when a button for changing the output set value of the electric knife 35a manufactured by A is pressed, the output set value of the electric knife 35a manufactured by A is up-dated. Thus, in order to reflect changed appliance information to the central control apparatus 19, the electric knife 35a manufactured by A transmits an update-appliance-information command to the conversion adapter 70 (indicated by C in FIG. 13).

The transmitted update-appliance-information command is received by the conversion adapter 70. In response to the receipt of the update-appliance-information command, the conversion adapter 70 transmits a positive response to the electric knife 35a manufactured by A as a response step.

At the same time, the conversion adapter 70 as a storage step stores the update-appliance-information command to the receive buffer of the second buffer. At that time, the control section 72 causes the appliance managing section 71 to store the update-appliance-information command as the latest value. Furthermore, the conversion adapter 70 as a communication data transmission step transmits the stored update command to the central control apparatus 19.

The central control apparatus 19 updates the appliance information in the appliance information managing section 40 based on the received update-appliance information command. The GUI display/operation processing section 41 causes the operation panel 18 to display the updated appliance information. Then, the central control apparatus 19 transmits the positive response to the conversion adapter 70 with respect to the received update-appliance-information command.

In this way, when the appliance information of the central control apparatus 19 is updated by the update-appliance-information command, the central control apparatus 19 transmits a check-appliance information command to the conversion adapter 70 at a predetermined time, such as every 100 ms, defined by the first protocol so that the appliance information stored in the central control apparatus 19 is not different from the current appliance information of the electric knife 35a manufactured by A.

The check-appliance-information command is received by the conversion adapter 70. In response to the receipt of the check-appliance-information command, the conversion adapter 70 causes to check whether any difference exists from the latest value in the appliance information managing section 71. Furthermore, as a step of checking a difference from the value of the electric knife 35a manufactured by A, the conversion adapter 70 transmits the appliance information stored in the first buffer to the electric knife 35a manufactured by A.

When the electric knife 35a manufactured by A receives the transmitted updated appliance information by the periodical polling at intervals of 200 ms based on the second protocol, the sequence involved in the update of the appliance information indicated by C in FIG. 13 ends. After that, the periodical polling by the electric knife 35a manufactured by A and conversion adapter 70 is continuously performed.

The exchange of appliance information may be the exchange of appliance information of all functions of one appliance or the exchange of appliance information of a specific function.

As described above, the conversion adapter according to the present embodiment can convert the interface and protocol of each medical appliance to the interface and protocol of the central control apparatus, and the communication between the central control apparatus and a medical appliance connected thereto can be efficiently performed.

When a new medical appliance is connected to the central control apparatus, the conversion adapter according to the present embodiment does not have to change a common command definition of the category that the appliance belongs to. Thus, the burden on the development of software in the central control apparatus can be reduced.

Since the common command definition has a reservation part of a variable length, lower data can be extended easily for the function expressed by the higher data.

Furthermore, the conversion adapter of the present embodiment causes the first and second buffers to store received communication data and transmits the communication data at a predetermined time. Thus, the difference in communication speed between a first protocol and a second protocol can be absorbed.

The conversion adapter of the present embodiment operates with the central control apparatus as if the conversion adapter communicates with a connected medical appliance. On the other hand, the conversion adapter operates with each medical appliance as if the conversion adapter communicates with the central control apparatus.

Furthermore, because of the conversion adapter of the present embodiment, the central control apparatus may have a unified communication I/F port, which can reduce the complexity of the configuration and the size of the central control apparatus.

Having described the category, "Electric Knife", especially, the electric knife 35a manufactured by A, the communication between the central control apparatus and a medical appliance even belonging to the other categories or to a different category "Electric Knife" can be performed efficiently with the same configuration as that of the electric knife 35a manufactured by A.

Having described that the conversion adapter 70 has only one communication I/F to which a medical appliance is to be connected, multiple kinds of communication I/F may be provided thereto. In this case, the conversion adapter 70 has a common command definition and a unique command definition corresponding to an appliance connecting thereto.

Second Embodiment

Next, a medical system of a second embodiment will be described.

In the medical system of the second embodiment, a central control apparatus in a central control room can centrally manage appliances placed in various places within a hospital over a network connecting the central control apparatus in the central control room and the appliances, that is, a so-called in-hospital network.

In a conventional medical system, the central control apparatus is placed in a place where the appliances are used and is connected to the appliances. Therefore, changing the appliance connecting to the central control apparatus complicates the wiring, which is a problem.

The medical system of the present embodiment employs the conversion adapter of the first embodiment and allows the easy change of the configuration and wiring of the appliances in various places by converting various interfaces and protocols to a predetermined interface and protocol. Efficient communication without delay can be implemented by using the conversion adapter of the first embodiment.

First of all, a schematic configuration of a medical system 100 of the present embodiment will be described. FIG. 14 is a schematic configuration diagram of the medical system 100.

The medical system 100 is an in-hospital network built in a hospital, as shown in FIG. 14. The medical system 100 connects a central control room, multiple operation rooms and places including the reception over a line 106. For simple description, two operation rooms of an operation room A and an operation room B are provided.

The central control room includes a management PC 101, a central management monitor 102, a PC slot 103, multiple PC modules 104 and a connection switching portion 105. The operation room A includes a conversion adapter 70a, a conversion adapter 70b, a connector 107, a hub 108, a trolley 109a, a trolley 109b, an operation unit 110, and a client PC 111. The operation room B includes a connector, a conversion adapter and a trolley. The reception has a client PC.

The management PC 101 in the central control room and the connection switching portion 105 are connected to the line 106 such as Ethernet. The connection switching portion 105 is connected to the multiple PC modules 104. The PC modules 104 are connected to the PC slot 103, and the PC slot 103 is connected to the central management monitor 102.

The conversion adapters 70a and 70b of the present embodiment have multiple communication I/Fs. The appliances in the trolley 109a in the operation room A are respectively connected to the conversion adapter 70a. The conversion adapter 70a is connected to the line 106 through the hub 108 and connector 107.

The appliances in the trolley 109b are respectively connected to the conversion adapter 70b. The operation unit 110 such as a Personal Digital Assistance (PDA) is connected to the conversion adapter 70b.

Like the conversion adapter 70a, the conversion adapter 70b is also connected to the line 106 through the hub 108 and connector 107. The client PC 111 in the operation room A is connected to the line 106 through a connector.

The appliances in the trolley in the operation room B are connected to the conversion adapter. The conversion adapter is connected to the line through a connector in the operation room.

The client PC at the reception is also connected to the line 106 through a connector at the reception.

In the medical system 100 having such a configuration, the management PC 101 and central management monitor 102 in the central control room obtain and distribute medical information, appliance information and voice information, for example, from the appliances in the medical system 100 such as the trolley, client PC and operation unit for the central management.

The PC module 104 can use another PC module if one of them has a problem. Each PC module may correspond to one room.

Communication data may delay in this case. However, according to the second embodiment, the conversion adapter 70a and conversion adapter 70b temporarily store the communication data and transmit a response signal to the other party when they receive data. Thus, efficient communication can be performed.

As described above, the medical system 100 of the present embodiment can resolve the complexity of the wiring layout and can simplify the configuration of the appliance placed in each operation room. Furthermore, since the control section is placed at one place of the central control room, the maintenance is also easier. Furthermore, the switchability among PC modules can address a failure in one PC module without changing the connection of an appliance within an operation room.

The medical system of the present embodiment can perform efficient communication by using above-described conversion adapter even when a delay occurs in communication data.

Third Embodiment

Next, a medical system of a third embodiment will be described.

The medical system of the third embodiment increases the communication efficiency not by the parallel processing on the transfer formats of common and unique commands as in the first embodiment but by the serial processing.

According to the first embodiment, as shown in FIG. 7, a common command and a unique command are defined, and a command transmitted by a different protocol and in a different format from a connected appliance is categorized as a common command if the safety standards for the ways of operations and/or display are close, which unifies the processing of the central control apparatus and increases the development efficiency. On the other hand, a command, which is not common, is handled as a unique command and is subject to the ways of operations and/or display specific for the function thereof.

In other words, in order to communicate, the ID of an appliance, for example, is first identified, and a common command and a unique command are used appropriately within the range of the appliance.

On the other hand, according to the present embodiment, the ID of an appliance is first identified, and the function is categorized based on the common command. On a communication path, a sequence is defined in accordance with the value defined by the ID and common command of the appliance.

First, upon communication connection, the other party is identified by the appliance ID, and a table stored in the central control apparatus and the converter is read out. After that, in the communication processing, exchanges are performed with the common command. For example, the common commands may include a set value command, synchronization command, measured value command, initial setting command and check-status command of an electric knife. In order to perform communication processing, a sequence is defined under the categories. The converter allocates a unique command, such as a mode-conversion command, which is obtained from an electric knife to the set value command of the common command. In this case, one or more unique commands may be allocated within the common commands. The converter transmits a common command to the central control apparatus based on a predetermined sequence, and the central control apparatus reads out and interprets the unique command allocated within the common command based on the table.

Thus, the communication processing of the central control apparatus can be implemented only with an appliance ID and a common command, and the type of a unique command is not required to recognize, which simplifies the communication processing. Apparently, even without the converter therebetween, an electric knife may be directly connected to the central control apparatus, and the communication path may allow simple exchanges with a common command.

According to the first embodiment, defining a common command based on the function to some extent allows the sequence processing in accordance with the function and, at the same time, the flexible extension against a change in set range and/or change in operation method. On the other hand, according to the third embodiment, the common command part is further abstracted, and the communication processing is simplified independently of a unique command on a communication sequence. Therefore, a change in set range, change in operation method and addition or deletion of a function can be flexibly addressed.

Fourth Embodiment

Next, a medical system of a fourth embodiment will be described.

In the medical system of the fourth embodiment, a converter automatically absorbs a difference in protocol and communicates with a central control apparatus by a common protocol.

According to the first embodiment, one or more appliances with different protocols are connected to the converter. For example, appliances with a same connector form but with different protocols must be detected, and the protocols must be converted to a common protocol.

For example, when the electric knife 35a manufactured by A and the electric knife 35b manufactured by B shown in FIG. 5 have a same connector form but different protocols, a supported protocol is pre-stored in the converter, and the connection of the connector is detected based on a hardware signal (such as open connector). After that, the protocols are detected sequentially. By setting time-out in a connection sequence, the connection by the next protocol is attempted if no connection is identified within a predetermined period of time, and the connection is established. Thus, the connections of the electric knife 35a manufactured by A and the electric knife 35b manufactured by B are confirmed, and the information on the connected appliances can be provided.

In this case, the data structures are also different naturally since the protocols are different. The converter only extracts the data part of a unique command at predetermined times of the electric knife 35a manufactured by A and the electric knife 35b manufactured by B. A structure block associated with a common command (where a command is defined if only one piece of data is extracted while a structure block is defined if multiple functions are extracted) can be transmitted to the central control apparatus by a common protocol. With the structure block, the appliance information managing section 71 is not required, and commands stored in a time series in the first and second buffers can be transmitted/received collectively. Furthermore, the values within the structure block can be interpreted at desired timings. Thus, control can be performed thereover efficiently.

According to the present embodiment, two paths for a common command and a unique command are prepared like the first embodiment, and the structure block as in the fourth embodiment and the command for a function as in the first embodiment may be transferred independently of each other.

For example, a common command is transferred from a connected appliance by a unified protocol in a predetermined format. For example, the allocation of a protocol (as in the first embodiment) requiring a sequence for checking whether a connected appliance has been really changed in response to the change of a function from the central control apparatus allows the transfer of the function command and the check of the status of the connected appliance (by performing polling to check all statuses periodically, for example) by using a common structure block. Furthermore, when one unique command is transferred for one function and when a simple protocol that does not perform status check on a connected appliance is allocated, the function can be easily added.

According to the fourth embodiment, a common protocol format is adopted in accordance with the characteristics of multiple different protocols connecting to the converter or central control apparatus, and multiple formats or sequences such as a common command and a unique command may be adopted for the conversion in accordance with the characteristic of the protocol to be converted, which allows easier management.

Apparently, the function to be exchanged by a unique command may be easily allocated in a structure block of common commands.

The invention is not limited to the above embodiments, and changes may be made thereto without departing from the spirit and scope of the invention.

What is claimed is:

1. A conversion adapter for connecting a control apparatus that controls a medical appliance and the medical appliance, the adapter comprising:
a first communication unit for performing communication with the control apparatus based on a first protocol;
a second communication unit for performing communication with the medical appliance based on a second protocol;
a data extracting unit for extracting communication data from a data signal based on function information associating the data signal received through the first communication unit and the second communication unit and a function of the medical appliance;
a first storage unit for storing the communication data received from the control apparatus based on the first protocol;
a second storage unit for storing the communication data received from the medical appliance based on the second protocol; and
a control unit for transmitting the communication data stored in the first storage unit to the medical appliance through the second communication unit, transmitting the communication data stored in the second storage unit to the control apparatus through the first communication unit and further transmitting a response signal to the medical appliance through the second communication unit when the communication data is received through the second communication unit.

2. The conversion adapter according to claim 1, wherein:
the function information includes:
common function information associating the data signal and a common function in the multiple medical appliances; and
unique function information associating the data signal and a unique function to the medical appliance.

3. The conversion adapter according to claim 2, wherein the second protocol is RS-232C protocol.

4. The conversion adapter according to claim 2, wherein the medical appliance is an electric knife.

5. The conversion adapter according to claim 4, wherein the second protocol is RS-232C protocol.

6. The conversion adapter according to claim 1, wherein;
the control unit obtains the communication data from the control apparatus at a predetermined timing based on the first protocol and updates the communication data stored in the first storage unit.

7. The conversion adapter according to claim 6, wherein the second protocol is RS-232C protocol.

8. The conversion adapter according to claim 6, wherein the medical appliance is an electric knife.

9. The conversion adapter according to claim 8, wherein the second protocol is RS-232C protocol.

10. The conversion adapter according to claim 1, wherein the medical appliance is an electric knife.

11. The conversion adapter according to claim 10, wherein the second protocol is RS-232C protocol.

12. A medical system including a conversion adapter for connecting a control apparatus that controls a medical appliance and the medical appliance,
wherein the conversion adapter includes:
a first communication unit for performing communication with the control apparatus based on a first protocol;
a second communication unit for performing communication with the medical appliance based on a second protocol;
a data extracting unit for extracting communication data from a data signal based on function information associating the data signal received through the first communication unit and the second communication unit and a function of the medical appliance;
a first storage unit for storing the communication data received from the control apparatus based on the first protocol;
a second storage unit for storing the communication data received from the medical appliance based on the second protocol; and
a control unit for transmitting the communication data stored in the first storage unit to the medical appliance through the second communication unit, transmitting the communication data stored in the second storage unit to the control apparatus through the first communication unit and further transmitting a response signal to the medical appliance through the second communication unit when the communication data is received through the second communication unit.

13. The medical system according to claim 12, wherein the medical appliance is an electric knife.

14. The medical system according to claim 13, wherein the second protocol is RS-232C protocol.

15. The medical system according to claim 12, wherein the second protocol is RS-232C protocol.

16. A communication method in a conversion adapter for connecting a control apparatus that controls a medical appliance and the medical appliance, the method comprising:
a response step of transmitting a response signal to the medical appliance through when communication data is received from the medical appliance;
a communication data storage step of storing the communication data;
a communication data transmission step of transmitting the stored communication data to the control apparatus;
an appliance data storage step of storing appliance data when the appliance data is received from the control apparatus; and
an appliance data transmission step of transmitting the stored appliance data to the medical appliance at a predetermined timing based on a second protocol.

17. The communication method according to claim 16, wherein the medical appliance is an electric knife.

18. The communication method according to claim 17, wherein the second protocol is RS-232C protocol.

19. The conversion adapter according to claim 1, wherein the second protocol is RS-232C protocol.

20. The communication method according to claim 16, wherein the second protocol is RS-232C protocol.

* * * * *